US009668686B2

(12) United States Patent
Feldman et al.

(10) Patent No.: US 9,668,686 B2
(45) Date of Patent: Jun. 6, 2017

(54) IN VIVO GLUCOSE SENSING IN AN INCREASED PERFUSION DERMAL LAYER

(71) Applicant: ABBOTT DIABETES CARE INC., Alameda, CA (US)

(72) Inventors: Benjamin Jay Feldman, Berkeley, CA (US); Hyun Cho, Berkeley, CA (US); Austin Leach, Oakland, CA (US); John Charles Mazza, Long Beach, CA (US)

(73) Assignee: ABBOTT DIABETES CARE INC., Alameda, CA (US)

(*) Notice: Subject to any disclaimer, the term of this patent is extended or adjusted under 35 U.S.C. 154(b) by 471 days.

(21) Appl. No.: 14/173,619

(22) Filed: Feb. 5, 2014

(65) Prior Publication Data

US 2014/0275907 A1    Sep. 18, 2014

Related U.S. Application Data

(60) Provisional application No. 61/800,828, filed on Mar. 15, 2013.

(51) Int. Cl.
  *A61B 5/00* (2006.01)
  *A61B 5/1491* (2006.01)
  *A61B 5/145* (2006.01)

(52) U.S. Cl.
  CPC ........ *A61B 5/1491* (2013.01); *A61B 5/14503* (2013.01); *A61B 5/14532* (2013.01)

(58) Field of Classification Search
  CPC .............. A61B 5/1491; A61B 5/14503; A61B 5/14532
  USPC ........................................ 600/345, 347, 365
  See application file for complete search history.

(56) References Cited

U.S. PATENT DOCUMENTS

| | | | |
|---|---|---|---|
| 6,240,306 B1 | 5/2001 | Rohrscheib et al. | |
| 6,706,049 B2 | 3/2004 | Moerman | |
| 7,509,153 B2 | 3/2009 | Blank et al. | |
| 2004/0096959 A1 | 5/2004 | Stiene et al. | |
| 2004/0162573 A1* | 8/2004 | Kheiri | A61B 5/150022 606/182 |
| 2004/0249254 A1* | 12/2004 | Racchini | A61B 5/0002 600/347 |
| 2005/0054908 A1 | 3/2005 | Blank et al. | |
| 2007/0197957 A1 | 8/2007 | Hunter et al. | |
| 2009/0259118 A1 | 10/2009 | Feldman et al. | |
| 2010/0312314 A1 | 12/2010 | Ice et al. | |
| 2011/0144463 A1 | 6/2011 | Pesach et al. | |
| 2011/0213225 A1* | 9/2011 | Bernstein | G06Q 50/22 600/309 |

(Continued)

FOREIGN PATENT DOCUMENTS

| | | |
|---|---|---|
| WO | WO 2005/035017 A2 | 4/2005 |
| WO | WO 2008/114224 A2 | 9/2008 |

OTHER PUBLICATIONS

WO, PCT/US14/14930 ISR, Apr. 24, 2014.

(Continued)

*Primary Examiner* — Tiffany Weston
(74) *Attorney, Agent, or Firm* — One LLP

(57) ABSTRACT

Systems, devices, and methods are provided that enable the sensing of an analyte level within, e.g., the dermal layer of the skin of a subject. These systems, devices, and methods can utilize modalities that increase perfusion in an area local to a dermal sensor.

19 Claims, 11 Drawing Sheets

(56) References Cited

U.S. PATENT DOCUMENTS

2012/0078071 A1    3/2012   Bohm et al.
2012/0296187 A1   11/2012   Henning et al.
2014/0171771 A1    6/2014   Feldman et al.

OTHER PUBLICATIONS

EP, 14765185.5 Extended Search Report, Sep. 9, 2016.
WO, PCT/US2014/014930 IPRP, Sep. 15, 2015.
Ali, S., "Finite Element Modeling of Dermally-Implanted Enzymatic Microparticle Glucose Sensors", Thesis Submitted to the Office of Graduate Studies of Texas A&M University, Oct. 21, 2011, retrieved from https://oaktrust.library.tamu.edu/handle/1969.1/ETD-TAMU-2010-08-8314, pp. 1-129.

* cited by examiner

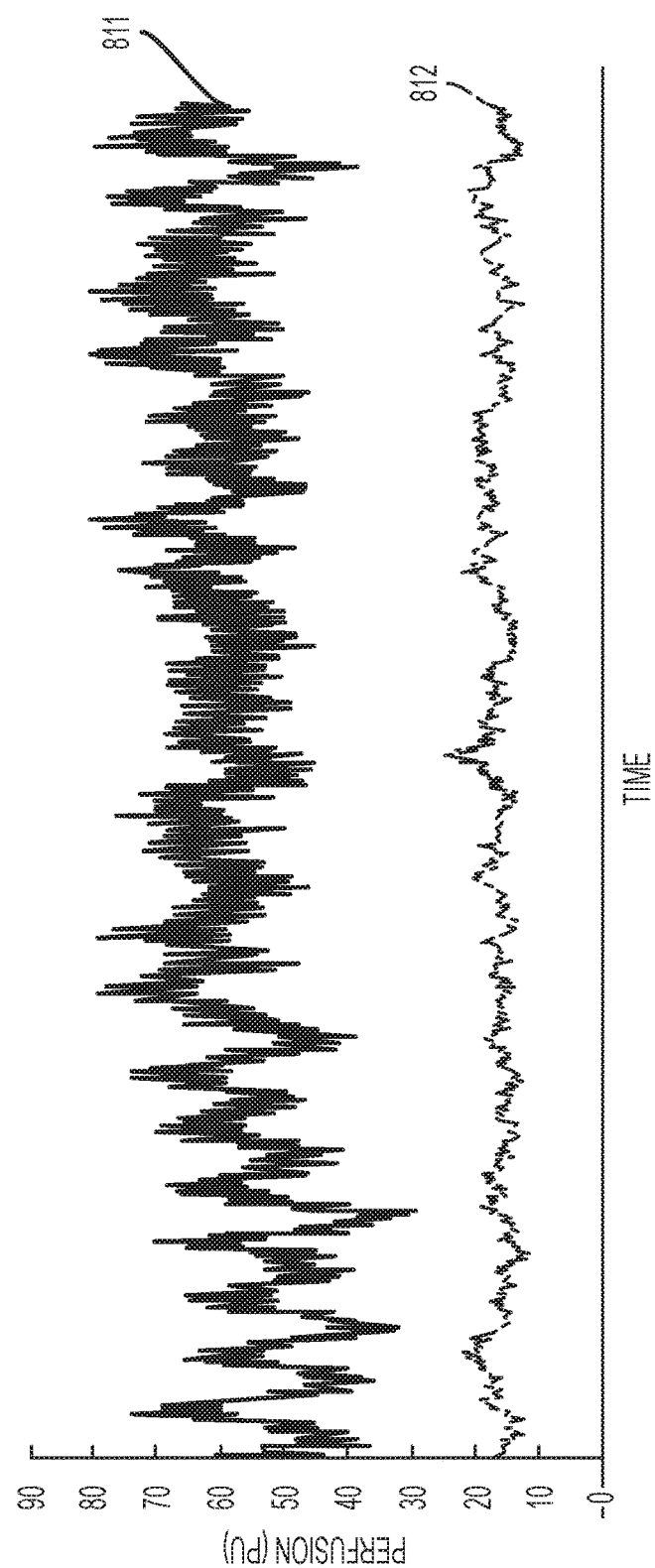

IN VIVO GLUCOSE SENSING IN AN INCREASED PERFUSION DERMAL LAYER

CROSS-REFERENCE TO RELATED APPLICATIONS

This application claims the benefit of and priority to U.S. Provisional Application No. 61/800,828, filed Mar. 15, 2013, and titled "In Vivo Glucose Sensing in an Increased Perfusion Dermal Layer," which is incorporated by reference herein in its entirety for all purposes.

FIELD

The subject matter described herein relates to systems, devices, and methods for the performance of in vivo analyte sensing in a subject.

BACKGROUND

The detection of the level of glucose or other analytes, such as lactate, oxygen or the like, in certain individuals is vitally important to their health. For example, the monitoring of glucose is particularly important to individuals with diabetes. Diabetics may need to monitor glucose levels to determine when insulin is needed to reduce glucose levels in their bodies or when additional glucose is needed to raise the level of glucose in their bodies.

Devices have been developed for the in vivo monitoring of analytes such as glucose in bodily fluid such as in the blood stream or in interstitial fluid over a period of time. These analyte measuring devices include in vivo analyte sensors that are positioned in vivo, e.g., below a skin surface of a user in a blood vessel or in the subcutaneous tissue of a user during the testing.

Blood vessel sensors are more invasive than subcutaneous sensors, but have the advantage of providing analyte concentrations directly from the blood. Subcutaneous analyte sensors are therefore used, but they too have certain limitations. For example, the insertion of the analyte sensor in the subcutaneous tissue results in skin and/or tissue trauma, which in turn provokes an immunological response that can cause inaccurate sensor readings, at least for a period of time. For example in the case of glucose sensors, the trauma may cause an over-consumption of glucose in the positioned sensor vicinity by erythrocytes released by localized bleeding. Further, the glucose response from a subcutaneously positioned sensor lags the response of a venously positioned sensor, primarily due to a physiological lag between subcutaneous and venous glucose.

It would therefore be desirable to have devices and methods that address these issues and that accurately monitor analyte levels, such as glucose, in areas of the body other than blood vessels or the subcutaneous tissue.

SUMMARY

Provided herein are example embodiments of in vivo dermal analyte sensors having a sensing portion for placement in, e.g., a dermal layer of a subject. Also provided are embodiments of sensor control devices that couple to and control the sensor, which are a component of more comprehensive in vivo analyte monitoring systems that enable processing and display of data obtained with the dermal sensor. Examples of methods of using the dermal sensor and the various related components, such as methods of determining in vivo analyte presence and concentration using the dermally-positioned in vivo dermal analyte sensors, are provided as well. Many of these embodiments have the conveniences and advantages of being operable when positioned in the dermal layer rather than in a blood vessel, and yet retain or improve upon the accuracy of a blood vessel sensor. For example, many of these embodiments do not exhibit the extent of physiological lag that is experienced by sensors positioned in the non-dermal, subcutaneous space.

In certain embodiments, in vivo dermal glucose sensing is performed at a local dermal site that has been modulated to increase perfusion at the site. A perfusion modulator can be integrated with a dermal sensor or a sensor control device, or may be a separate component or module. Heat, electrical current, pressure, surface features, and vasodilatory substances are but some of the example modalities provided herein to adjust perfusion.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIG. 8D is a graph depicting experimental results reflecting the perfusion beneath the example embodiment of FIGS. 8A-C.

DETAILED DESCRIPTION

Figure 1:
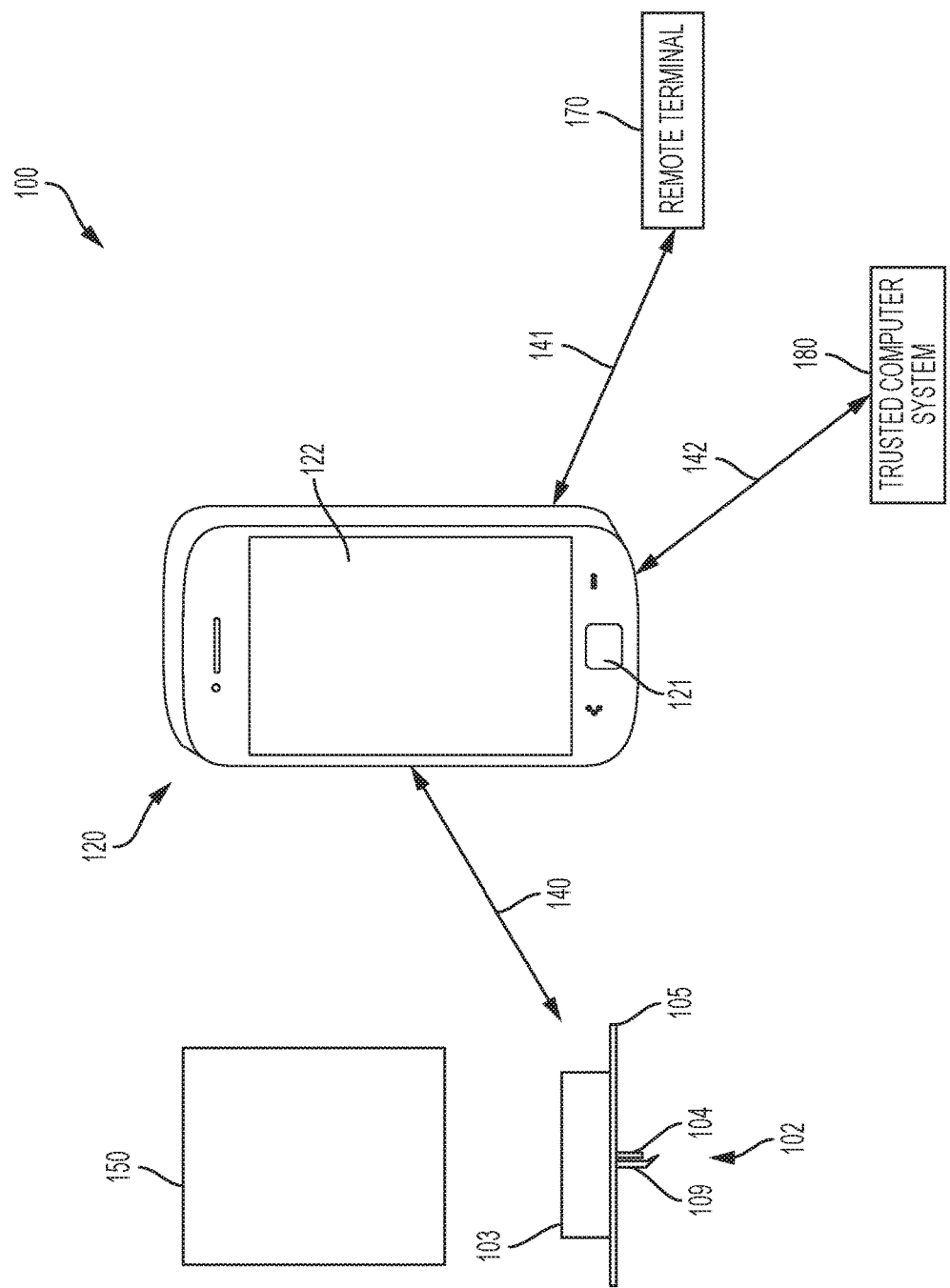
FIG. 1 is an illustrative view depicting an example embodiment of an in vivo-based analyte monitoring system.

Before the systems, devices, and methods of the present disclosure are described in greater detail, it is to be understood that they are not limited to those particular embodiments described, as such may, of course, vary. It is also to be understood that the terminology used herein is for the purpose of describing the embodiments, and is not intended to be limiting, since the scope of the systems, devices, and methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the sensor and applicator devices and methods. The upper and lower limits of these smaller ranges may independently be included in the smaller ranges and are also encompassed within the devices and methods, subject to any specifically excluded limit in the stated range. Where the stated range includes one or both of the limits, ranges excluding either or both of those included limits are also included in the devices and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the systems, devices, and methods belong. Although any systems, devices, and methods similar or equivalent to those described herein can also be used in the practice or testing of the described embodiments, representative illustrative systems, devices, and methods are now described.

All publications and patents cited in this specification are herein incorporated by reference as if each individual publication or patent were specifically and individually indicated to be incorporated by reference and are incorporated herein by reference to disclose and describe the sensor and applicator devices, methods and/or materials in connection with which the publications are cited. The citation of any publication is for its disclosure prior to the filing date and should not be construed as an admission that the present devices and methods are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or the use of a "negative" limitation.

It is appreciated that certain features of the devices and methods, which are, for clarity, described in the context of separate embodiments, may also be provided in combination in a single embodiment. For example, increased perfusion can be accomplished by combining two or more of the current-based, heat-based, chemical-based, and pressure-based approaches described herein. Conversely, various features of the devices and methods, which are, for brevity, described in the context of a single embodiment, may also be provided separately or in any suitable sub-combination. All combinations of the embodiments are specifically embraced by the present devices and methods and are disclosed herein just as if each and every combination was individually and explicitly disclosed, to the extent that such combinations embrace operable processes, devices, systems, and/or kits. In addition, all sub-combinations listed in the embodiments describing such variables are also specifically embraced by the present devices and methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present devices and methods. Any recited method can be carried out in the order of events recited or in any other order which is logically possible.

An issue with conventional in vivo analyte monitoring systems designed to determine analyte concentration in interstitial fluid (ISF) of the subcutaneous space is that there is a substantial time lag that exists between the ISF analyte concentration and the blood analyte concentration. This is the case when the monitored analyte is glucose, and for other analytes whose concentration changes quickly. (Glucose will be used primarily as an exemplary analyte herein, but it is to be understood that other analytes may be monitored.) For example, a time lag in the distribution of glucose from blood to the interstitium has been observed. As a result of this lag, ISF glucose concentrations do not correlate exactly with blood glucose concentrations at a given point in time.

Sites that are highly perfused tend to experience reduced lag. Unfortunately, the most highly perfused sites (such as finger tips, palms, and the face) are not very convenient for sensor positioning. Sites that are inherently highly perfused tend to have a high concentration of blood vessels and nerve endings, and sensor insertion tends to be relatively more painful there than other sites. Sensor insertion in highly perfused sites can also result in relatively more bleeding. These can be significant drawbacks. Thus, it is desirable to have or create highly perfused sensing sites that are not subject to these drawbacks.

It has been learned that—as compared to traditional in vivo analyte monitoring systems which determine ISF analyte concentrations in subcutaneous tissue (e.g., 3 mm to 10 mm beneath the surface of the skin)—in vivo monitoring of dermal fluid (e.g., 0.5 mm to 3 mm) analyte concentration provides analyte concentration data with markedly reduced lag times as compared to blood analyte concentration (e.g., venous glucose). Accordingly, analyte concentration data obtained using a dermal analyte sensor correlates more closely to the analyte concentration in blood as compared to in vivo ISF sensors.

Despite the advantages afforded by measuring analyte concentrations in dermal fluid, significant technical hurdles exist with respect to the insertion of one or more sensor components, e.g., a working electrode, into and no deeper than a dermal layer of a subject. For example, the significantly reduced scale of the sensor component(s) necessary for a dermal sensor as compared to an ISF/subcutaneous sensor renders the dermal sensing components extremely fragile and therefore more susceptible to breaking under the modest forces exerted on the sensor by the skin surface and/or underlying tissue as the sensor is being inserted.

As such, monitoring the concentration of an analyte in the dermal layer of a subject requires more than simply scaling down the size of an ISF/subcutaneous analyte sensor. New strategies for inserting dermal analyte sensors and components thereof are needed. Technical challenges of sensors sized for dermal sensing are also significant. For example, sensors must be sized so that they are only positionable in the dermal layer, but must also be able to provide acceptable current densities, stabilities, and sensitivities, in addition to being manufacturable with any consistency and reliability, e.g., by high speed manufacturing techniques. Examples of sensors, sensor applicator sets, and methods that address many of the aforementioned challenges are described in U.S. Patent Appl. Publ. 2009/0259118, filed Mar. 31, 2009, and U.S. patent application Ser. No. 14/108,964, filed Dec. 17, 2013, both of which are incorporated by reference herein in their entirety for all purposes. All of the systems, devices, and methods described in these incorporated applications are suitable for use with the embodiments described herein.

As mentioned, dermal glucose sensing exhibits less physiological lag than in vivo subcutaneous glucose devices and methods, and therefore dermal sensing of glucose more accurately reflects the gold standard of venous blood glucose. While not being tied to any particular theory, the inventors believe that the improved performance of in vivo dermal glucose sensing is attributed to the generally superior perfusion of the dermis layer (e.g., 0.5-3 mm depth below the skin surface) as compared to the subcutaneous fat layer (e.g., 3 or more mm depth below the skin surface). However, it is known that dermal perfusion is variable, and that this variability is related to the skin's role as a thermo-regulatory barrier. In certain embodiments the inventors have determined to use that variability to their advantage, to actively modulate the perfusion of a localized site in the neighborhood of an implanted sensor.

Accordingly, systems, devices, and methods are disclosed that increase cutaneous perfusion so that dermal sensing of glucose from these sites reflects even more closely the gold standard of the venous blood glucose, as opposed to dermal sites that are not modulated to increase perfusion. These disclosed systems, devices, and methods also increase perfusion in a consistent, reliable, and controlled manner. Generally, the disclosed systems, devices, and methods allow for the dermal sensing of glucose (or other analyte(s)) from a dermal site at which perfusion has been increased to a level that is greater than its natural perfusion state, i.e., a perfusion-modulated site.

In Vivo Analyte Monitoring Systems

Before describing the techniques for increasing dermal perfusion, it is helpful to describe example embodiments of the in vivo analyte monitoring systems with which those techniques can be used. In vivo analyte monitoring systems can be differentiated from "in vitro" systems that contact a biological sample outside of the body (or rather "ex vivo") and typically include a meter device that has a port for receiving an analyte test strip carrying bodily fluid of the user, which can be analyzed to determine the user's blood sugar level.

FIG. 1 is an illustrative view depicting an example of an in vivo-based analyte monitoring system 100 having a sensor control device 102 and a reader device 120 that communicate with each other over a local communication path (or link) 140, which can be wired or wireless, and uni-directional or bi-directional. In embodiments where path 140 is wireless, a near field communication (NFC) protocol, RFID protocol, Bluetooth or Bluetooth Low Energy protocol, Wi-Fi protocol, proprietary protocol, or the like can be used.

Reader device 120 is also capable of wired, wireless, or combined communication with a remote computer system 170 over communication path (or link) 141 and with trusted computer system 180 over communication path (or link) 142. Communication paths 141 and 142 can be part of a telecommunications network, such as a Wi-Fi network, a local area network (LAN), a wide area network (WAN), the internet, or other data network for uni-directional or bi-directional communication. In an alternative embodiment, communication paths 141 and 142 can be the same path. All communications over paths 140, 141, and 142 can be encrypted and sensor control device 102, reader device 120, remote computer system 170, and trusted computer system 180 can each be configured to encrypt and decrypt those communications sent and received.

Sensor control device 102 can include a housing 103 containing in vivo analyte monitoring circuitry and a power source (see, e.g., device 102 as described in the '225 Publication incorporated below). The sensor control device, and variations thereof, can also be referred to as a "sensor control unit," an "on-body electronics" device or unit, an "on-body" device or unit, or a "sensor data communication" device or unit, to name a few.

The in vivo analyte monitoring circuitry of the sensor control device 102 is electrically coupled with a dermal sensor 104 that extends through an adhesive patch 105 and projects away from housing 103. Adhesive patch 105 contains an adhesive layer (not shown) for attachment to a skin surface of the body of the user. (Other forms of attachment to the body may be used, in addition to or instead of adhesive.) Sensor 104 is adapted to be at least partially inserted into the body of the user, where it can make contact with that user's dermal fluid. Sensor 104 is used, along with the in vivo analyte monitoring circuitry, to determine an analyte level of the user. That analyte level can be communicated, e.g., displayed, to the user and/or otherwise incorporated into a diabetes monitoring regime. Dermal fluid is a clear fluid that is found in the dermal layer of the skin. This fluid typically does not include blood, but can in some instances. The presence of blood can, however, temporarily detract from the accuracy of the measurements.

An insertion needle 109 can be optionally included to create the insertion path for dermal sensor 104. Here, insertion needle 109 is placed adjacent to dermal sensor 104 and a tip portion of insertion needle 109 is angled over dermal sensor 104. In another example embodiment, dermal sensor 104 can reside within a lumen, interior space, or groove of the insertion needle, e.g., such that both share a common central longitudinal axis. Dermal sensor 104 and insertion needle 109 can each be configured, and dermal sensor 104 can also be placed and oriented with respect to insertion needle 610, in any of the manners described in the incorporated application Ser. No. 14/108,964. For example, in any of the embodiments described herein, insertion needle 109 can have or can lack an interior space (such as a lumen or cut-out, etc.) and can have a bladed (having one or more beveled faces) or non-bladed tip (rounded and coming to a single pointed termination, not unlike a typical sewing needle). Alternatively, dermal sensor 104 can act as the needle itself, in which case a distinct insertion needle (other than sensor 104) can be omitted.

Sensor 104 and any accompanying sensor control electronics can be applied to the body in any desired manner. For example, also shown in FIG. 1 is an embodiment of insertion device 150 that, when operated, transcutaneously positions a portion of analyte sensor 104 through the user's skin and into contact with the bodily fluid, and positions sensor control device 102 with adhesive patch 105 onto the skin. In other embodiments, insertion device 150 can position sensor 104 first, and then the accompanying sensor control electronics can be coupled to sensor 104 afterwards, either manually or with the aid of a mechanical device.

Referring back to the portable reader device 120 of analyte monitoring system 100, this device 120, and variations thereof, can be referred to as a "reader device" (or simply a "reader"), "handheld electronics" (or a handheld), a "portable data processing" device or unit, a "data receiver," a "receiver" device or unit (or simply a receiver), or a "remote" device or unit, to name a few. Reader device 120 can receive sensed analyte data from the sensor control device and process and/or display that sensed analyte data, in any number of forms, to the user. Reader device 120 has a display 122 to output information to the user and/or to accept an input from the user (e.g., if configured as a touch screen), and one optional input component 121 (or more), such as a button, actuator, touch sensitive switch, capacitive switch, pressure sensitive switch, jog wheel or the like, to input data or commands to reader device 120 or otherwise control the operation of reader device 120.

In certain embodiments, display 122 and input component 121 may be integrated into a single component, for example a display that can detect the presence and location of a physical contact touch upon the display such as a touch screen user interface. In such embodiments, the user may control the operation of reader device 120 by utilizing a set of pre-programmed motion commands, including, but not limited to, single or double tapping the display, dragging a finger or instrument across the display, motioning multiple fingers or instruments toward one another, motioning multiple fingers or instruments away from one another, etc. In certain embodiments, a display includes a touch screen having areas of pixels with single or dual function capacitive elements that serve as LCD elements and touch sensors.

Reader device 120 can also include one or more data communication ports (not shown) for wired data communication with external devices such as a remote terminal, e.g., a personal computer. Example data communication ports include USB ports, mini USB ports, RS-232 ports, Ethernet ports, Firewire ports, or other similar data communication ports configured to connect to the compatible data cables.

Reader device 120 may also include an integrated or attachable in vitro glucose meter, including an in vitro test strip port (not shown) to receive an in vitro glucose test strip for performing in vitro blood glucose measurements.

Display 122 can be configured to display a variety of information—some or all of which may be displayed at the same or different time on display 122. The displayed information can be user-selectable so that a user can customize the information shown on a given display screen. Display 122 may include, but is not limited to, a graphical display, for example, providing a graphical output of glucose values over a monitored time period (which may show: markers such as meals, exercise, sleep, heart rate, blood pressure, etc.; a numerical display, for example, providing monitored glucose values (acquired or received in response to the request for the information); and a trend or directional arrow display that indicates a rate of analyte change and/or a rate of the rate of analyte change, e.g., by moving locations on display 122).

In certain embodiments, reader device 120 can be configured to output alarms, alert notifications, glucose values, etc., which may be visual, audible, tactile, or any combination thereof. In one aspect, reader device 120 may include other output components such as a speaker, vibratory output component and the like to provide audible and/or vibratory output indications to the user in addition to the visual output indication provided on display 122. Other devices such as personal computers have also been utilized with or incorporated into in vivo and in vitro monitoring systems.

After the positioning of sensor control device 102 on the skin surface and dermal sensor 104 in vivo to establish fluid contact with the dermal fluid, sensor control device 102 can be configured to wirelessly communicate analyte related data (such as, for example, data corresponding to monitored analyte level and/or monitored temperature data, and/or stored historical analyte related data) when sensor control device 102 receives a command or request signal from reader device 120. In certain embodiments, sensor control device 102 may be configured to at least periodically broadcast real time data associated with monitored analyte level which is received by reader device 120, when reader device 120 is within communication range of the data broadcast from sensor control device 102, e.g., it does not first need a command or request from reader device 120 to send that information.

In certain other embodiments, reader device 120 may be configured to transmit one or more commands to sensor control device 102 to initiate data transfer, and in response, sensor control device 102 may be configured to wirelessly transmit stored analyte related data collected during the monitoring time period to reader device 120.

Reader device 120 may in turn be connected to remote terminal 170, such as a personal computer, which can be used by the user or a medical professional to display and/or analyze the collected analyte data. Reader device 120 may also be connected to a trusted computer system 180 that can be used for authentication of a third party software application. In both instances, reader device 120 can function as a data conduit to transfer the stored analyte level information from the sensor control device 102 to remote terminal 170 or trusted computer system 180. In certain embodiments, the received data from the sensor control device 102 may be stored (permanently or temporarily) in one or more memories of reader device 120.

Remote terminal 170 may be a personal computer, a server terminal, a laptop computer, a tablet, or other suitable data processing device. Remote terminal 170 can be (or include) software for data management and analysis and communication with the components in analyte monitoring system 100. Operation and use of remote terminal 170 is further described in the incorporated '225 Publication. Analyte monitoring system 100 can also be configured to operate with a data processing module (not shown), also as described in the incorporated '225 Publication.

Trusted computer system 180 can include one or more computers, servers, networks, databases, and the like. Trusted computer system 180 can be within the possession of the manufacturer or distributor of sensor control device 102, either physically or virtually through a secured connection, and can be used to provide software updates for sensor control device 102 and reader device 120 and/or can be used for other functions that require interface with the manufacturer of system 100 (or a component thereof). These functions can also be performed indirectly via remote terminal 170.

The processing of data within system 100 can be performed by one or more control logic units or microprocessors of reader device 120, remote terminal 170, trusted computer system 180, and/or sensor control device 102. Such information may be displayed at these locations in any of the formats already described herein.

This information may be utilized by the user to determine any necessary corrective actions to ensure the analyte level remains within an acceptable and/or clinically safe range. Other visual indicators, including colors, flashing, fading, etc., as well as audio indicators, including a change in pitch, volume, or tone of an audio output, and/or vibratory or other tactile indicators may also be incorporated into the outputting of trend data as means of notifying the user of the current level, direction, and/or rate of change of the monitored analyte level. For example, based on a determined rate of glucose change, programmed clinically significant glucose threshold levels (e.g., hyperglycemic and/or hypoglycemic levels), and current analyte level derived by an in vivo analyte sensor, an algorithm stored on a computer readable medium of system 100 can be used to determine the time it will take to reach a clinically significant level and can be used to output a notification in advance of reaching the clinically significant level.

Reader device 120 can be a mobile communication device such as a mobile telephone including, but not limited to, a Wi-Fi or internet enabled smart phone, tablet, or personal digital assistant (PDA). Examples of smart phones can include those mobile phones based on a Windows® operating system, Android™ operating system, iPhone® operating system, Palm® WebOS™, Blackberry® operating system, or Symbian® operating system, with data network connectivity functionality for data communication over an internet connection and/or a local area network (LAN).

Reader device 120 can also be configured as a mobile smart wearable electronics assembly, such as an optical assembly that is worn over or adjacent to the user's eye (e.g., a smart glass or smart glasses, such as Google glasses, which is a mobile communication device). This optical assembly can have a transparent display that displays information about the user's analyte level (as described herein) to the user while at the same time allowing the user to see through the display such that the user's overall vision is minimally obstructed. The optical assembly may be capable of wireless communications similar to a smart phone. Other examples of wearable electronics include devices that are worn around or in the proximity of the user's wrist (e.g., a watch, etc.), neck (e.g., a necklace, etc.), head (e.g., a headband, hat, etc.), chest, or the like.

In vivo analyte monitoring systems 100 include "Continuous Analyte Monitoring" systems (or "Continuous Glucose Monitoring" systems) that can broadcast data from sensor control device 102 to reader device 120 continuously without prompting, i.e., automatically according to a broadcast schedule, and also include "Flash Analyte Monitoring" systems (or "Flash Glucose Monitoring" systems or simply "Flash" systems) that can transfer data from sensor control device 102 in response to a scan or request for data by reader device 120, such as with an NFC or RFID protocol. In vivo analyte monitoring systems 100 can also operate without the need for finger stick calibration.

Modulation of Dermal Perfusion

Referring back to perfusion in the dermal layer, generally speaking, the detection of the presence and/or concentration of glucose from a dermal site having increased perfusion is disclosed. Also disclosed are embodiments for modulating perfusion at a dermal site, where the modulation can increase perfusion at the site to a level that is greater than the level of perfusion without such modulation. Perfusion can be increased dramatically at a perfusion-modulated site relative to the non-modulated site. Increases can range, e.g., from 10% to 1000%. Perfusion increase may be measured by, for example, Doppler perfusion monitoring. While the present embodiments are described in the context of increasing perfusion in the dermal layer, these embodiments can also be adapted to increase perfusion at other layers as well, such as the subcutaneous layer.

A number of mechanisms can be implemented to increase cutaneous perfusion, including but not limited to the application of heat (local heating of the skin, e.g., to 40 C), the application of electric current (e.g., 0.1 mA/cm$^2$ for 5 minutes/hour), the application of vasostimulatory compounds (e.g., capsaicin), and the application of mechanical pressure (e.g., by way of contours on the underlying surface of the sensor's base). The present embodiments include those that can apply these stimuli to increase perfusion in the dermis, but not in the deeper subcutaneous fat. These mechanisms can be separate from or combined with an in vivo dermal glucose sensor to produce a dermal glucose sensor that senses glucose by increasing the local cutaneous perfusion in the direct vicinity of the sensor.

Increase of Dermal Perfusion Through Local Heating

Devices and methods of applying heat to the skin surface can be used to increase perfusion at the dermal layer adjacent the heated area. In one example, temperatures of approximately 40° C. can be applied, for example to an area of about one cm$^2$, for a time period of two minutes or more. In certain embodiments, the perfusion at the dermal site can be modulated by heat to a six-fold increase in perfusion at the site within about two minutes, as measured by laser Doppler perfusion monitoring. The heat can be highly localized, such that an area of one cm$^2$ or less can be heated. In many cases, the increase in perfusion caused by the local heat will last for twenty minutes to an hour after the heating has ceased. In certain embodiments, local perfusion can be increased by pulsatile heating, whereby the heat is applied intermittently, minimizing the battery requirements for the associated heater.

Figure 2:
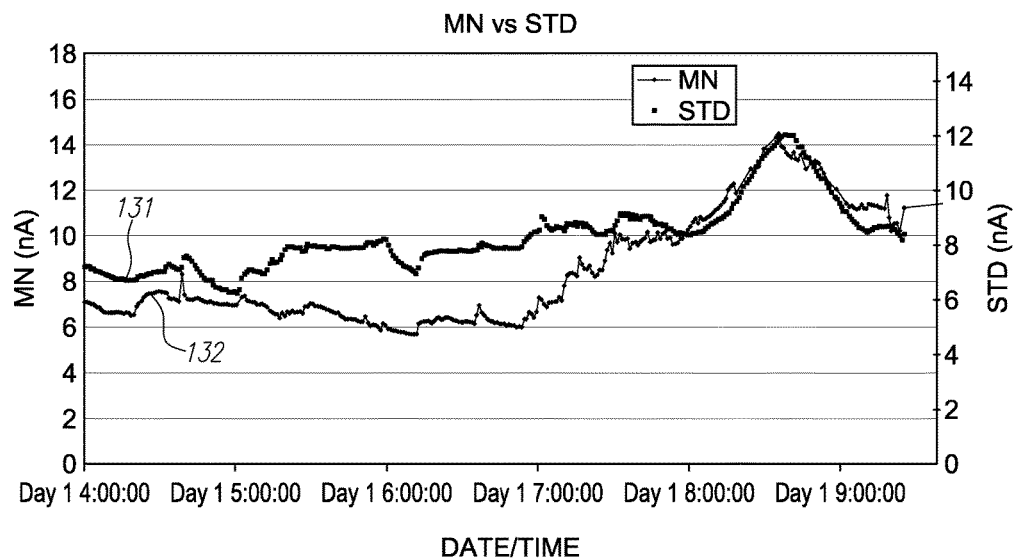
FIG. 2 is a graph depicting experimental analyte results obtained from an in vivo subcutaneous sensor positioned in the subcutaneous layer and an in vivo dermal sensor positioned in the dermal space.

FIG. 2 is a graph depicting an example of increased dermal perfusion through applied heat. As a comparison, a subcutaneous glucose sensor was positioned in the forearm, and its reference, counter and working electrode leads were attached to a multistat-logger. Simultaneously, a dermal glucose sensor (working electrode only, e.g., as described in U.S. patent application Ser. No. 12/416,126, filed Mar. 31, 2009) was positioned in the forearm about six inches distant from the positioned subcutaneous sensor, to a depth of about one mm. The dermal working electrode was connected to the same multistat-logger as the subcutaneous sensor, such that the reference and counter electrodes of the subcutaneous sensor also functioned as reference and counter for the dermal sensor. A sample six-hour period from these two sensors, incorporating a morning meal, is shown in FIG. 2, which shows that the graph of the subcutaneous sensor (curve 131) and the graph of the dermal sensor (curve 132). Concerning the meal at 8 am, there is little difference in response between the two sensors. The dermal sensor appears to lead slightly as glucose increases.

Next, heat was applied to the dermal site to increase perfusion at the site. An ankle heat wrap about 2×4 inches in area was inserted in a protective sleeve and placed on the skin over the dermal working electrode. The heat wrap included iron particles, designed to generate heat by reaction with oxygen, along with various other materials to regulate the rate of reaction. The heat wrap provides a temperature of 40° C. or higher for up to 8 hours. The heat from the heat wrap did not extend to the subcutaneous sensor.

Figure 3:
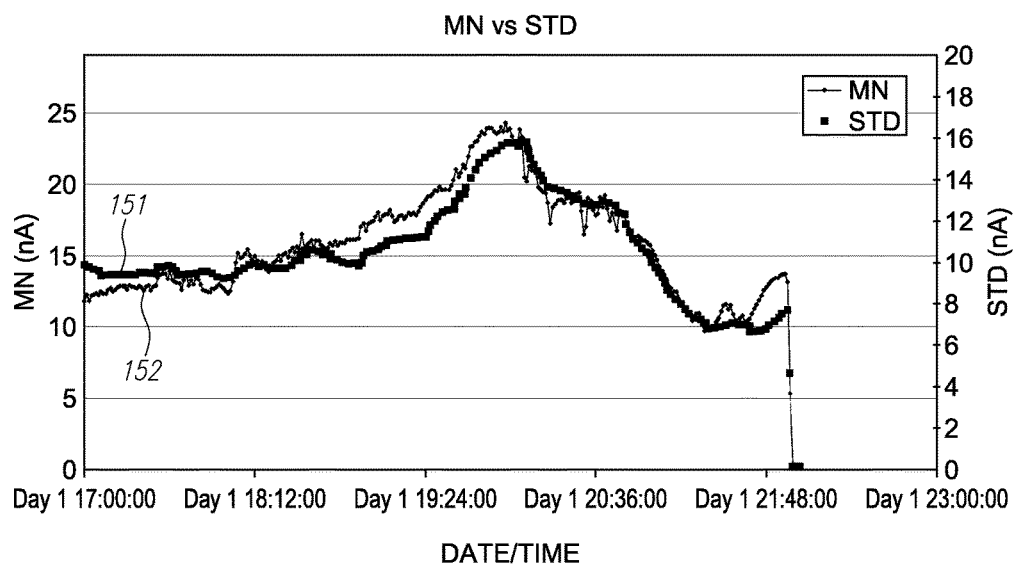
FIG. 3 is a graph depicting experimental analyte results of the in vivo subcutaneous sensor and the in vivo dermal sensor of FIG. 1, but which has been perfusion-modulated by heat so that it has increased perfusion to at the dermal site.

Application of this local heat changed the performance of the dermal sensor, as shown in FIG. 3. Concerning the meal that commences at about 6 pm (18:00), the dermal sensor (curve 152) now leads the subcutaneous sensor (curve 151) substantially, by 8-10 minutes on the rising edge of the meal peak. It is apparent that the applied heat increased the perfusion in the neighborhood of the dermal sensor, causing it to react more quickly to the meal peak than the subcutaneous sensor.

Dermal perfusion can be increased in small areas by the application of small area heaters. Heaters can be radially disposed around a dermal sensor, with a total heated area of one $cm^2$ or less. A heater(s) can be battery powered from the attached glucose sensor electronics. It can also be a disposable chemical disk, based on, e.g., iron particles, with a lifetime of 8-24 hours, and it can be periodically replaced.

Figure 4:
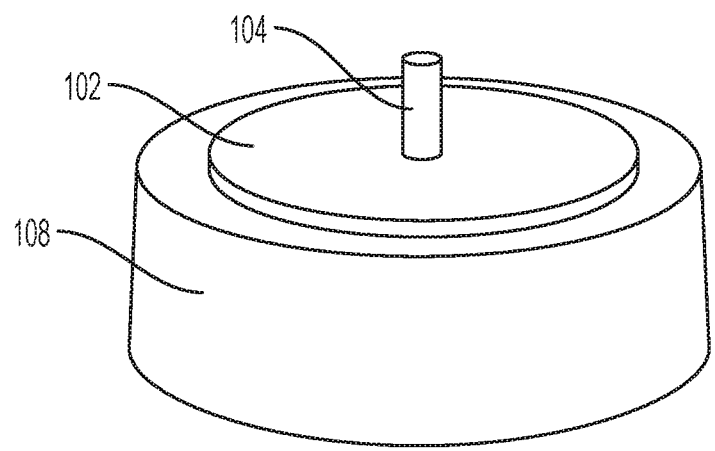
FIG. 4 depicts an embodiment of a perfusion modulation glucose sensing device that includes an in vivo glucose dermal sensor and an integrated heating unit configured to apply controlled heat to a dermal site to increase perfusion at the site.

FIG. 4 shows an embodiment of dermal sensor 104 as part of dermal sensor control device 102 coupled with an integrated heater 108, which can convert electrical energy into heat. Heater 108 can be connected to an external power supply or can utilize a power supply of sensor control device 102.

Increase of Dermal Perfusion Through the Application of Electrical Current

In some embodiments, the application of current (such as might be appropriate for iontophoresis) to small areas on the skin surface can be used to increase the localized effects of the cutaneous perfusion (a result that was experimentally confirmed). The amount of current may be modest, for example as might be appropriate for iontophoresis. For example, currents of 0.1 $mA/cm^2$ applied with a duty cycle of about 5%, may be used.

In one example, 0.1 $mA/cm^2$, can be applied to a one $cm^2$ area on the forearm, abdomen, or the like, for one minute, to cause local cutaneous perfusion to increase by a factor of eight (as measured by laser Doppler flow meter in the region 0.5-1 mm below the skin surface). Cutaneous flow can be greatly increased, by a factor of seven, 20 minutes after the one minute application of current.

Figure 5A:
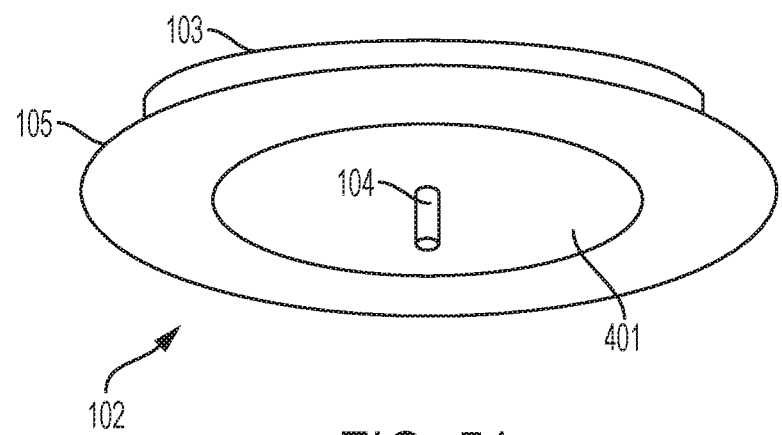
FIG. 5A is a schematic view depicting an example embodiment of a sensor control device with part of a current application unit.

Therefore, dermal sensor 104 could be coupled to a current application unit (e.g., contained partially within housing 103 and patch 105 of FIG. 1) for applying current to the skin. FIG. 5A is a schematic view depicting an example embodiment of sensor control device 102 with part of the current application unit (e.g., a conductive surface) 401 radially disposed around dermal sensor 104, with an area of about one $cm^2$ or less, at or near the surface of patch 105. Unit 401 can include a water-wet sponge or hydrogel for making skin contact coupled to an electrode (typically the cathode) for application of 0.1 $mA/cm^2$.

Another electrode/sponge combination of similar area (the anode) can be located on the skin, remote from dermal sensor 104, to complete the current path.

Increase of Dermal Perfusion Through the Application of Vasodilatory Substances

In certain embodiments, the application of vasodilatory substances to the skin can be used to increase perfusion. Vasodilatory substances include capsaicin, camphor, menthol, nitric oxide, vasoactive intestinal peptide (VIP), substance P, histamine, and vasodilator prostanoids 5. Therefore, dermal sensor 104 and/or patch 105 (or a base of device 102) can be coupled with a vasodilatory substance so that the substance is applied to the skin when the dermal sensor is positioned in the dermal layer. For example, the adhesive on patch 105 can include the vasodilatory substance and/or dermal sensor 104, itself, can be coated with the vasodilatory substance.

Figure 5B:
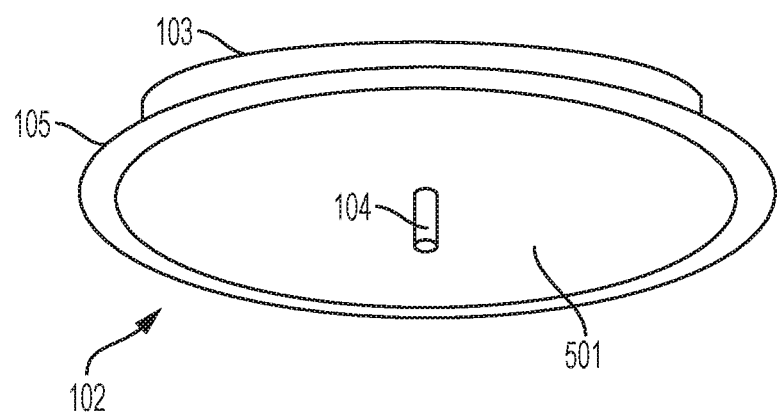
FIG. 5B is a schematic view depicting an example embodiment of a sensor control device having a time release pad for the application of a vasodilatory substance.

FIG. 5B is a schematic view depicting an example embodiment of sensor control device 102 with a time-release pad 501 radially disposed around dermal sensor 104. The vasodilatory substance might be applied from time-release pad 501 that is or is part of patch 105, such that a near-constant supply of the vasodilator is applied to the skin surface over the lifetime of sensor control device 102 when sensor 104 is positioned in the dermal layer (e.g., a sensor wear period of 14 days). Alternatively, the vasodilatory substance is not integrated with sensor 104, but rather manually applied by the subject his or herself. In any of these examples, the vasodilatory substance can be applied to the skin in a relatively small area (e.g., one $cm^2$) around dermal sensor 104.

Increase of Dermal Perfusion Through the Application of Mechanical Pressure

In certain embodiments, pressure locally applied to the skin can be used to increase perfusion, an effect referred to as pressure-induced vasodilation (PIV). Depicted in FIGS. 6A-B, 7A-B, 8A-C, and 9A-C, are example embodiments of sensor control devices 102 that include one or more perfusion-inducing pressure surface features positioned on the underside of the generally planar base 620 (e.g., patch 105) of each device 102. The one or more surface features can apply a local pressure to the skin in the direct vicinity of the dermal sensor. The shape and dimensions of the surface feature can vary to stimulate the most effective PIV in the dermis surrounding an inserted sensor.

Generally speaking, and without being tied to a particular theory, PIV can occur as a result of the myogenic response in the vasculature that is responsible for maintaining the transmural pressure across a vessel wall. When a vessel wall is acted upon by an external pressure (such as one applied by a sensor control device 102 residing mainly on the external surface of the skin), the myogenic response acts to increase the local blood flow in order to maintain the vessel lumen. For an increasing applied pressure, there exists a maximum for which the myogenic response can compensate, after which the internal pressure will decrease to physiological zero as the lumen is occluded.

The surface feature imposes a sufficient pressure to induce the maximum attainable perfusion via the myogenic response, but not so significant as to cause decreased perfusion due to vessel occlusion. This approach to locally modify perfusion is desirable since it is passive, in that it does not require thermal or electrical stimulation to the skin, each of which require an external or internal power source.

Referring back to FIGS. 6A-B, 7A-B, 8A-C, and 9A-C, views of a number of embodiments of sensor control devices 102 are shown. Each of these embodiments has one or more protrusions extending from the skin facing side of device 102 (e.g., which, in certain embodiments, can be a patch 105 or other adhesive-carrying member).

In these embodiments, although there are exceptions, generally the widest dimension (e.g., diameter along the X axis) of the center-most protrusion is adjacent base 620, and the width of protrusion 601 decreases (or remains constant) as traveling away (along the Y axis) from the skin facing surface 106 of base 620.

Figure 6A:
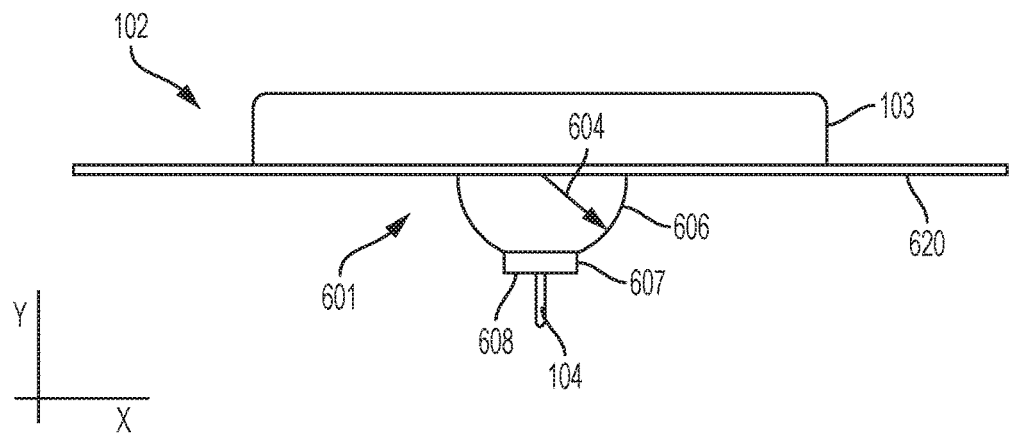
FIGS. 6A-B and 7A-B depicting example embodiments of a sensor control device having a protrusion for applying pressure to increase dermal perfusion.
Figure 6B:
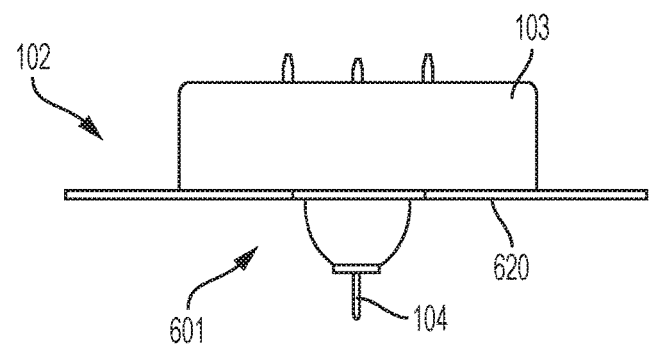

In the example embodiments of FIGS. 6A-B, a protrusion 601 can have a hemispherical or pseudo-hemispherical shape. FIG. 6A is a schematic illustration depicting a side view of an example embodiment of a sensor control device 102 with a single pseudo-hemispherical protrusion 601. FIG. 6B depicts a side view of another example embodiment of sensor control device 102 with a pseudo-hemispherical protrusion 601. In these embodiments, protrusion 601 has a substantially hemispherical surface, e.g., a surface with a generally constant radius 604 as measured from a central point, at a base (or proximal) portion 606 adjacent surface 106. Those of skill in the art will readily recognize those surfaces that qualify as hemispherical, as well as those that are substantially hemispherical.

The hemispherical base portion 606 can be optionally truncated and flattened at the distal side (away from surface 106). Here, a cylindrical or substantially cylindrical surface 607 with a flat (uncurved) distal face 608 is present, such that flat face 608 has the appearance of being stepped distally away from the hemispherical base portion. The height of cylindrical surface 607 is approximately one-sixth of the total height of protrusion 601, but other ratios can be used as well (one-fourth, one-fifth, one-seventh, and so forth). Face 608 could also be curved or have other surface features.

In this and all of the embodiments described herein, an insertion needle 109 can be mounted in the protrusion (e.g., 601) and/or base 620 and can extend away from the distal termination of the protrusion by a predetermined amount (e.g., 0.5 to 3.0 mm) that will create an insertion path for dermal sensor 104 (not shown) in the dermal layer. Dermal sensor 104 can be coupled with and extend from any analyte monitoring circuitry (not shown) contained within housing 103, through the protrusion, and away from the distal termination of the protrusion by the same or a lesser amount than needle 109. Dermal sensor 104 can be placed and oriented with respect to insertion needle 109 in any of the manners described in the incorporated application Ser. No. 14/108,964. Alternatively, dermal sensor 104 can act as the needle itself, in which case a distinct insertion needle (other than sensor 104) can be omitted.

Figure 7A:
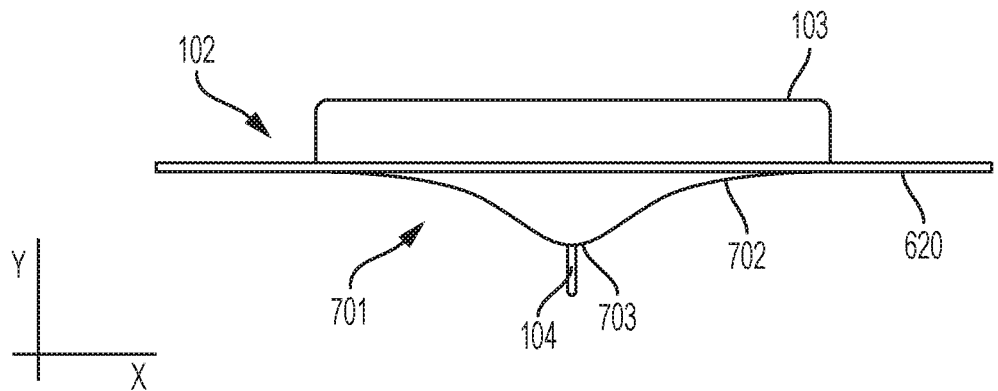
Figure 7B:
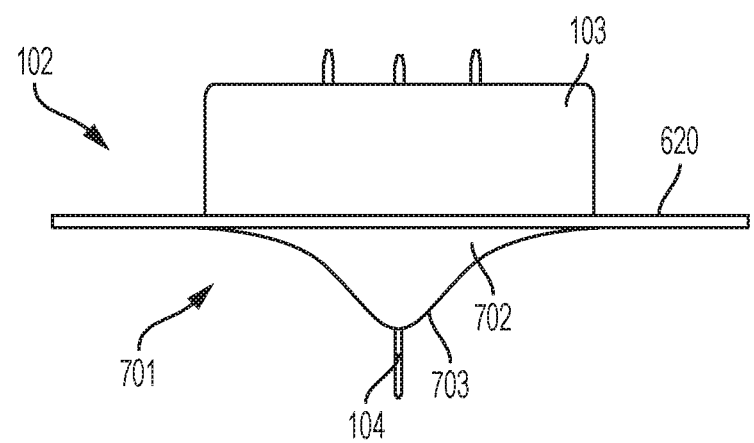

In the example embodiments of FIGS. 7A-B, a protrusion 701 can have a wave-like shape. FIG. 7A is a schematic illustration depicting a side view of an example embodiment of a single protrusion 701 with a wave-like shape and FIG. 7B depicts a side view of another example embodiment of protrusion 701 with a wave-like shape. In these embodiments, protrusion 701 has a cross-sectional shape (2D) with a profile that resembles a symmetric Gaussian distribution, such as a bell-curve (or substantially that of a bell-curve). Stated somewhat differently, protrusion 701 has a width that is greatest adjacent to base 620 and the width decreases at a decreasing rate as the distance (along the y-axis) from base 620 increases. When the slope of the surface of protrusion 701 reaches an angle of 30 or 45 degrees (or otherwise) the width continues to decrease but instead at an increasing rate as the distance from base 620 continues to increase, until projection 701 terminates. As a result, a surface 702 that is concave (or substantially concave) is present on each side of the portion of protrusion 701 adjacent base 620 (when viewed in cross-section) and, a surface 703 that is convex (or substantially convex) is present on the remaining portion of protrusion 701 that includes the termination of the protrusion. As the case with the embodiments of FIGS. 6A-B, protrusion 701 can be truncated or can include a stepped flat face (not shown) if desired.

Figure 7C:
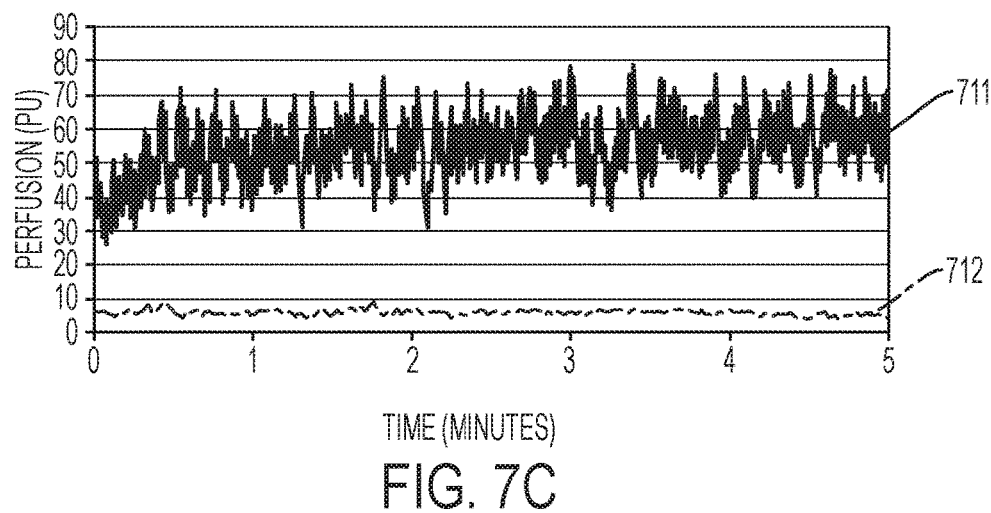
FIGS. 7C-D are graphs depicting experimental results reflecting the perfusion beneath an example embodiment of a sensor control device having a pressure-inducing protrusion.

FIG. 7C is a graph depicting experimental results reflecting the perfusion beneath an example embodiment of the wave-like protrusion 701 as measured over the course of three days (curve 711). Increased perfusion relative to the baseline (curve 712) was still observed on the third day.

Figure 7D:
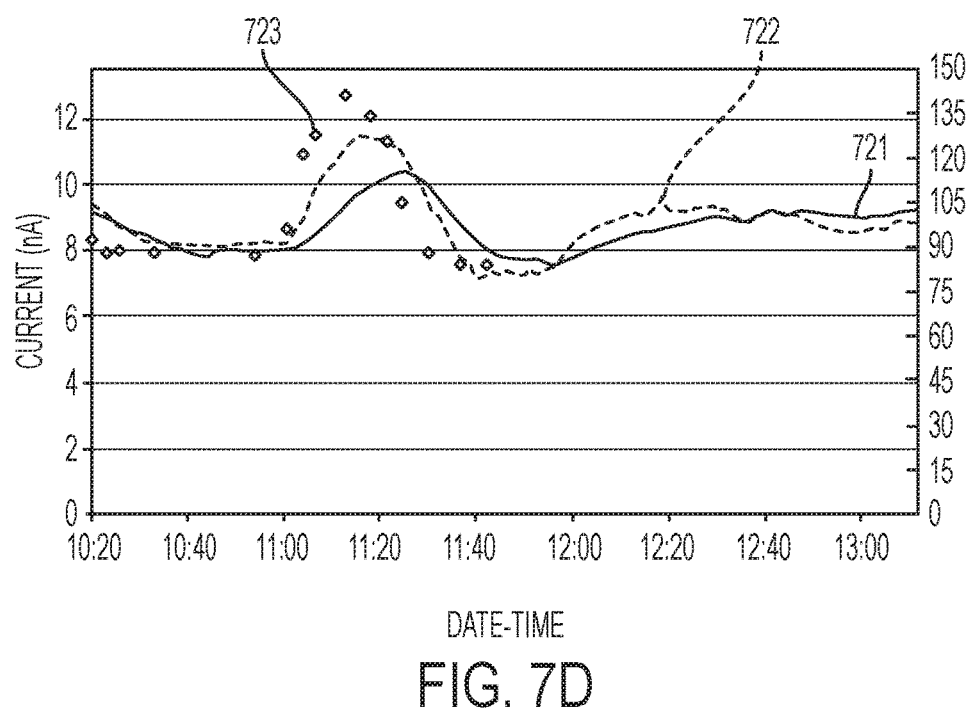

FIG. 7D is another graph depicting experimental results reflecting the analyte levels measured with an example embodiment of a dermal sensor 104 used with the wave-like protrusion 701 as compared to the analyte levels measured with a subcutaneous sensor and those measured with an in vitro meter (specifically finger-prick measurements). A subcutaneous sensor (that of a Navigator 1 device provided by Abbott Diabetes Care) was implanted in the upper arm. Reference, counter and working electrode leads were attached to a locally built multistat-logger. Simultaneously, a dermal sensor 104 with the wave-like protrusion 701 was implanted in the upper arm approximately one inch distant from the subcutaneous sensor, to a depth of about one mm. The dermal working electrode was connected to the same multistat-logger, such that the reference and counter electrodes of the subcutaneous sensor functioned as reference and counter for the dermal sensor also. A sample five hour period was measured from both the subcutaneous sensor (curve 721) and the dermal sensor (curve 722), incorporating a morning meal. Also shown are accompanying in vitro measurements (curve 723, taken with a Freestyle blood glucose monitoring device provided by Abbott Diabetes Care).

FIG. 7D shows that the dermal sensor results (722) lead those of the subcutaneous sensor (721) by a significant margin, and approach the in vitro results (723). It is apparent that the applied pressure from the wave-like protrusion 701 increased the perfusion in the neighborhood of the dermal sensor, causing it to react more quickly to the meal peak than the subcutaneous sensor.

Figure 8A:
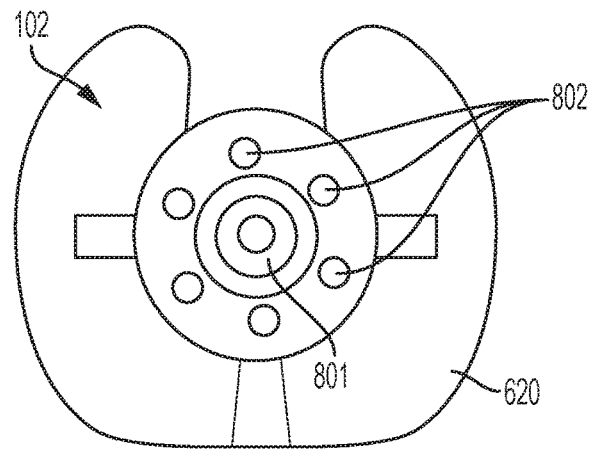
FIGS. 8A-C are bottom, perspective, and side views depicting another example embodiment of a sensor control device having multiple pressure-inducing protrusions.
Figure 8B:
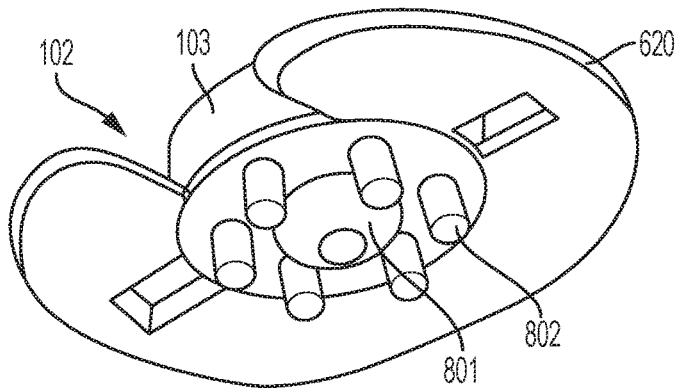
Figure 8C:
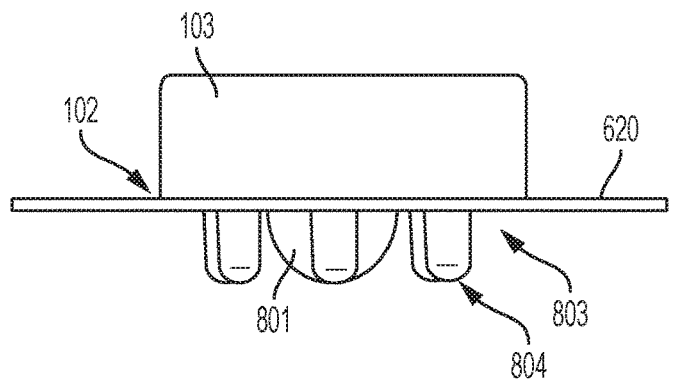

FIGS. 8A-C are bottom, perspective, and side views depicting another example embodiment of sensor control device 102, which in this case has multiple protrusions extending from base 620. Here, device 102 includes a hemispherical central projection 801 and multiple smaller, secondary projections 802 arranged at equal distances radially about and spaced apart from central projection 801. While there are six secondary projections 802, it should be noted that any number of one or more such projections can be used.

Hemispherical central projection 801 is similar to that described respect to FIGS. 6A-B but without the stepped cylindrical surface 607 and flat face 608. Each of the secondary projections 802 has a cylindrical or substantially cylindrical base portion 803 with a rounded or hemispherical terminal portion 804, giving them a post-like appearance, as best seen in FIGS. 8B-C. The distance from which projection 801 extends from base 620, i.e., its length, can be the same as, greater than, or less than the length of the secondary projections 802. Further, each of the secondary projections need not have the same length, which gives rise to a number of different variations in length between the secondary projections 802 and such a projection 801. In addition to this embodiment, secondary projections 802 can be used with any of the other embodiments described herein.

FIG. 8D is a graph 811 depicting experimental results reflecting the perfusion beneath an example embodiment of sensor control device 102 of FIGS. 8A-C as measured over the course of one day (curve 811). Increased perfusion exists relative to the baseline (curve 812) over the entire time period.

Figure 9A:
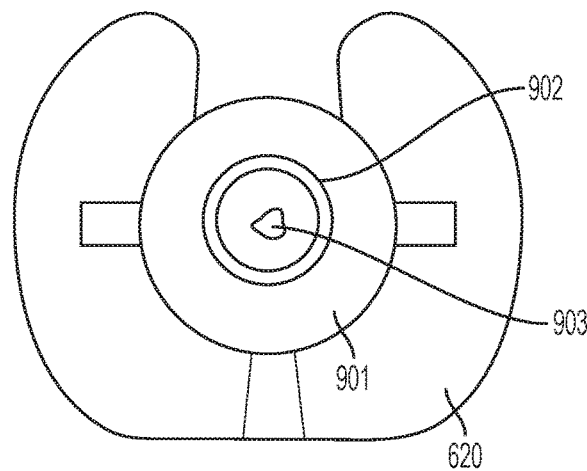
FIGS. 9A-C are bottom, perspective, and side views depicting another example embodiment of a sensor control device having a pressure-inducing protrusion.
Figure 9B:
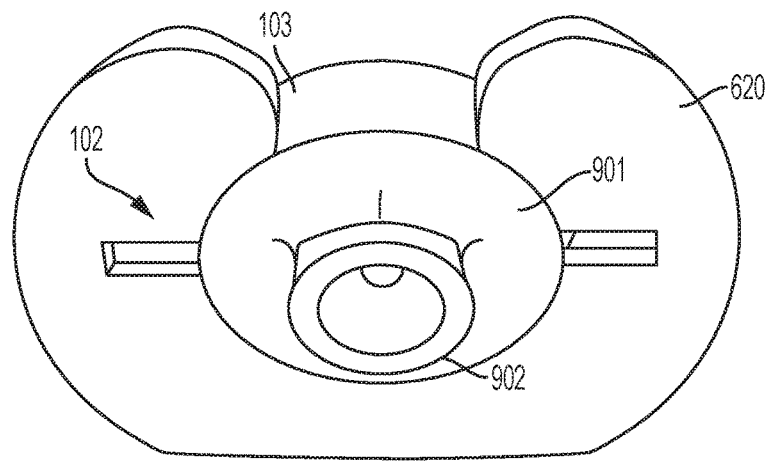
Figure 9C:
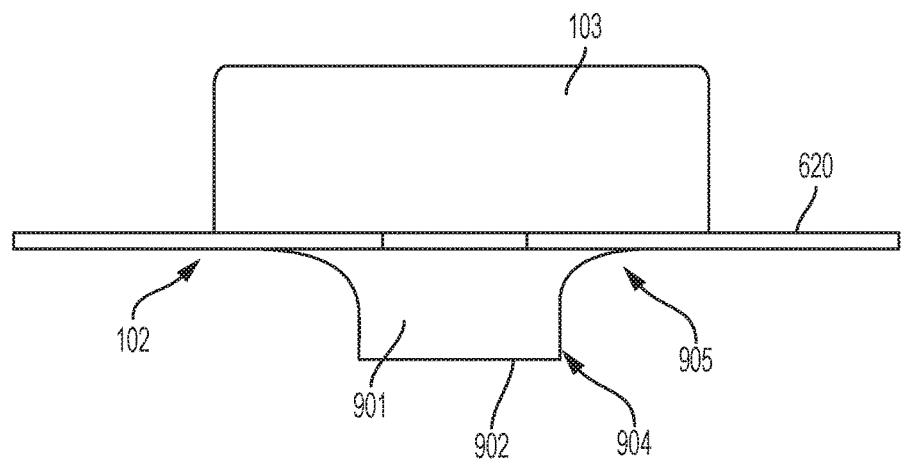

FIGS. 9A-C are bottom, perspective, and side views depicting another example embodiment of sensor control device 102, which in this case has a single protrusion 901 extending from base 620. Here, projection 901 includes a ring-like, or annular, termination 902 with sidewalls that are spaced apart from the opening 903 through which dermal sensor 104 (not shown) (and optionally needle 109) can extend. This results and the presence of a cavity that is wider than opening 903 and that can accommodate the presence of tissue between dermal sensor 104 and ring-like termination 902. As seen best in FIG. 9C, projection 901 has a cylindrical distal portion 904 and a concave or substantially concave proximal portion 905 that exists between base 620 and portion 904. Concave portion 905 gives projection 901 a gradually sloping transition between base 620 and the cylindrical sidewalls of portion 904.

Figure 9D:
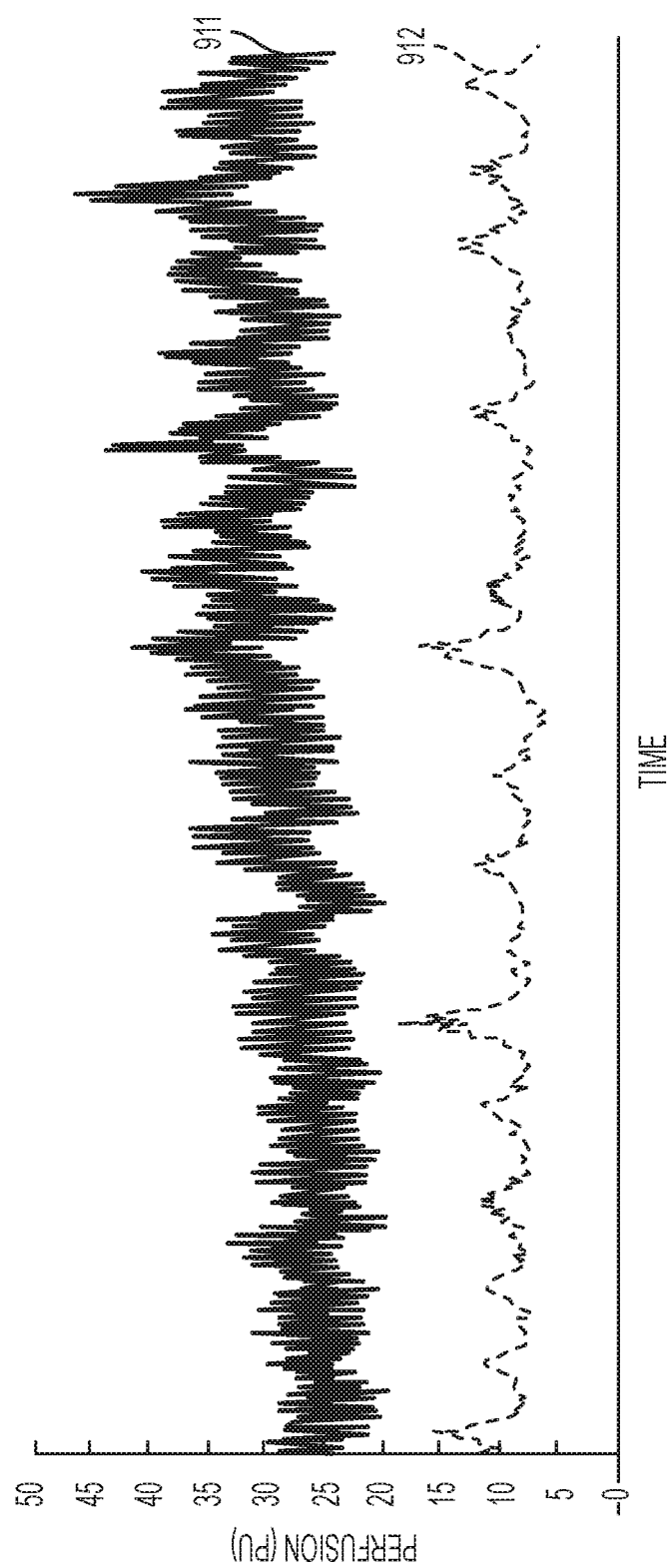
FIG. 9D is a graph depicting experimental results reflecting the perfusion beneath the example embodiment of FIGS. 9A-C.

FIG. 9D is a graph depicting experimental results reflecting the perfusion beneath an example embodiment of sensor control device 102 of FIGS. 9A-C as measured over the course of one day (curve 911). Increased perfusion exists relative to the baseline (curve 912) over the entire time period.

Controlled Application of Perfusion Modulation

The application of vasostimuli for increasing perfusion may be dynamically controlled in a number of ways. Vasostimuli in the form of energy (e.g., heat and current) can be controlled by turning the energy applicator on or off, or adjusting the relative energy output of the applicator (variable current, heat, etc.). A controllable dispenser (e.g., as part of sensor control device 102) or a time-release element can be used to vary the rate at which vasostimulatory chemicals are dispensed into contact with the skin. Similarly, a motor-controlled moveable element or another physically adjustable, enlargeable, or inflatable device can be used to control the application of pressure to the skin. In each of these examples control can be performed by software and/or electrical hardware associated with sensor control device 102.

The frequency and duration of the application of vasostimuli can be selected according to the needs of the application. For example, since vasodilatory effects can persist long after application of vasostimulation, that vasostimulation can be applied intermittently, e.g., such that a subsequent vasostimulatory pulse arrives before the original vasodilation has abated. In this way, a state of constant or near constant vasodilation can be maintained, with a relatively low duty cycle. Vasostimulatory application can occur according to a manufacturer-set or user-set schedule, or can be repeated in a regular fashion (e.g., 5%, 10%, 15%, or 20% of every time period, and so forth). The intermittent application of heat, for example, can be controlled with a thermometer and temperature feedback circuit to maintain a constant temperature.

In addition, since vasodilation is most desirable during intervals of rapidly changing glucose, all of the vasostimulatory embodiments can be initiated when the rate of change of the subject's monitored glucose level exceeds a threshold rate and, likewise, the vasostimulation can be ceased when the monitored glucose level falls below that rate of change (or a different one). For example vasostimulation might only be applied when the rate of glucose change exceeds 2 mg/dL/(min), or 1.5 mg/dL/min, or 1 mg/dL/(min), or less. This would have the effect of saving battery life, especially for energy intensive vasostimulatory means such as direct heating.

Further, the procedures described above might be combined, such that vaso-stimulatory pulses are applied at a preset frequency only when the rate of analyte change exceeds a certain rate, also preset.

Accuracy

According to certain embodiments, analyte concentrations as determined by the signals detected from a dermal analyte sensor from a dermal site that is perfusion modulated to increase perfusion according to the present disclosure are within +20% of a reference value such as a standard reference such as an in vitro test strip or YSI for glucose, such as within +15% of the reference value, including within +10% of the reference value, or within +5% of the reference value, or within +3% of the reference value, or within +2% of the reference value, or within +1% of the reference value. For example, for a given dermal sensor at a dermal site that is perfusion modulated to increase perfusion to the dermal site, at least 80% of analyte signal from the sensor collected over a 14 day wear period are within 80% of a reference value as determined by a standard reference such as an in vitro test strip or YSI for glucose, and embodiments include at least 90% of analyte signal from the sensor collected over a 14 day wear period are within 90% of a reference value, and at least 95%-100% of analyte signal from the sensor collected over a 14 day wear period are within 80%-100% of a reference value.

A large number of glucose measurement values obtained from increased perfusion dermal sites are within Zone A of the continuous glucose—error grid analysis (CG-EGA) by Clarke. For example, analyte measurement are within Zone A of the Clarke Error Grid Analysis for 75% or more of the analyte sensors, such as 80% or more, or 90% or more, including 95% or more, or 97% or more, or 99% or more of the analyte sensors. In certain instances, concentrations as determined by the signals detected from the dermal analyte sensor that are within Zone A or Zone B of the Clarke Error Grid Analysis. For example, dermal analyte concentrations as determined by the signals detected from the analyte sensor that are within Zone A or Zone B of the Clarke Error Grid Analysis for 75% or more of the analyte sensors, such as 80% or more, or 90% or more, including 95% or more, or 97% or more, or 99% or more of the analyte sensors.

Calibration

Due at least in part to the stability and accuracy of the devices and methods of the subject disclosure, the dermal sensors may require no active user calibration after being positioned in a perfusion modulated dermal site, or no more than one user calibration after positioned in a perfusion modulated dermal site. For example, a sensor may be factory calibrated and need not require further calibrating once dermally positioned and perfusion is increased. In the embodiments in which calibration by the user is required, the calibration may be according to a predetermined schedule or may be dynamic, i.e., the time for which may be determined by the system on a real-time basis according to various factors, such as but not limited to glucose concentration and/or temperature and/or rate of change of glucose, etc.

US Patent Application Publ. No. 2011/0213225 (the '225 Publication) generally describes components of an in vivo-based analyte monitoring system that are suitable for use with the system, device, and method embodiments described herein. The '225 Publication is incorporated by reference herein in its entirety for all purposes.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

Although the foregoing invention has been described in some detail by way of illustration and example for purposes of clarity of understanding, it is readily apparent to those of ordinary skill in the art in light of the teachings herein that certain changes and modifications may be made thereto without departing from the spirit or scope of the appended claims.

Accordingly, the preceding merely illustrates the principles of the devices and methods described herein. It will be appreciated that those skilled in the art will be able to devise various arrangements which, although not explicitly described or shown herein, embody the principles of the present subject matter and are included within its spirit and scope. Furthermore, all examples and conditional language recited herein are principally intended to aid the reader in understanding these principles and the concepts contributed by the inventors to furthering the art, and are to be construed as being without limitation to such specifically recited examples and conditions. Moreover, all statements herein reciting principles, aspects, and embodiments of the present subject matter as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present subject matter, therefore, is not intended to be limited to the exemplary embodiments shown and described herein, but rather by the claims submitted herewith and in the future.

What is claimed is:

1. An apparatus, comprising:
    a sensor insertable into a dermal layer of skin of a subject and adapted to sense an analyte level in the dermal layer;
    a base from which the sensor extends, the base being adapted to contact the skin of the subject with the sensor inserted into the dermal layer;
    an insertion needle; and
    a perfusion modulator adapted to increase perfusion in the dermal layer, wherein the perfusion modulator is at least one protrusion located on the base,
    wherein the at least one protrusion is adapted to apply pressure to increase perfusion in an area local to the sensor when inserted into the dermal layer, and
    wherein the insertion needle extends from the first protrusion adjacent to the sensor.

2. The apparatus of claim 1, wherein the at least one protrusion has a cross-sectional profile, the shape of the cross-sectional profile having a convex distal portion and concave proximal portions on both sides of the distal portion.

3. The apparatus of claim 1, wherein the at least one protrusion has a cross-sectional profile, the shape of the cross-sectional profile being substantially that of a bell-curve.

4. The apparatus of claim 3, further comprising a plurality of secondary protrusions.

5. The apparatus of claim 3, wherein the sensor extends from a distal termination of the at least one protrusion.

6. The apparatus of claim 1, wherein the insertion needle has an angled tip portion that extends over a distal termination of the sensor and is adapted to create an insertion path for the sensor.

7. The apparatus of claim 1, wherein the insertion needle does not have an interior space and has a pointed, non-bladed distal termination.

8. The apparatus of claim 1, wherein the at least one protrusion comprises a hemispherical proximal portion and a cylindrical distal portion.

9. The apparatus of claim 1, wherein the at least one protrusion comprises a first protrusion having a hemispherical portion and a plurality of secondary protrusions.

10. The apparatus of claim 9, wherein the plurality of secondary protrusions are arranged radially about and spaced apart from the hemispherical portion of the first protrusion.

11. The apparatus of claim 1 wherein the at least one protrusion comprises a first protrusion having a cylindrical distal portion and a gradually sloping proximal portion that is located between the base and the cylindrical distal portion.

12. The apparatus of claim 11, wherein the cylindrical distal portion defines a cavity that surrounds an opening from which the sensor extends.

13. The apparatus of claim 1, further comprising electrical circuitry adapted to control the sensor.

14. The apparatus of claim 13, further comprising:
    a power supply; and
    a housing that houses the electrical circuitry and the power supply.

15. The apparatus of claim 1, further comprising communication hardware for communicating data to a reader device.

16. The apparatus of claim 1, wherein the sensor comprises a sensing portion that is positioned to extend between 0.5 and 3.0 mm into the skin.

17. The apparatus of claim 1, wherein the analyte is glucose.

18. The apparatus of claim 1, further comprising:
    a processor adapted to control the sensor, wherein the sensor is adapted to sense a glucose level in the dermal layer;
    RFID circuitry adapted to wirelessly communicate data indicative of a sensed glucose level to a reader device;
    a power supply; and
    a housing that houses the processor, the RFID circuitry, and the power supply.

19. The apparatus of claim 1, further comprising:
    a processor adapted to control the sensor, wherein the sensor is adapted to sense a glucose level in the dermal layer;

Bluetooth circuitry adapted to wirelessly communicate data indicative of a sensed glucose level to a reader device;
a power supply; and
a housing that houses the processor, the Bluetooth circuitry, and the power supply.

* * * * *